United States Patent [19]

Miller et al.

[11] Patent Number: 5,106,987
[45] Date of Patent: * Apr. 21, 1992

[54] PROCESS FOR PREPARATION OF FLUOROMETHYL-SUBSTITUTED PYRIDINE DICARBOXYLATES

[75] Inventors: William H. Miller, Glendale; Mitchell J. Pulwer, St. Louis, both of Mo.

[73] Assignee: Monsanto Company, St. Louis, Mo.

[*] Notice: The portion of the term of this patent subsequent to Oct. 8, 2008 has been disclaimed.

[21] Appl. No.: 652,854

[22] Filed: Feb. 8, 1991

Related U.S. Application Data

[63] Continuation-in-part of Ser. No. 495,174, Mar. 19, 1990, abandoned.

[51] Int. Cl.$^5$ .............................................. C07D 211/82
[52] U.S. Cl. ............................................................. 546/321
[58] Field of Search .......................................... 546/321

[56] References Cited

U.S. PATENT DOCUMENTS

| | | | |
|---|---|---|---|
| 4,618,679 | 10/1986 | Lee | 546/220 |
| 4,692,184 | 9/1987 | Lee | 71/94 |
| 4,876,393 | 10/1989 | Heine et al. | 568/415 |

Primary Examiner—Mary C. Lee
Assistant Examiner—Lenora Miltenberger
Attorney, Agent, or Firm—Grace L. Bonner; Stanley M. Tarter; Howard C. Stanley

[57] ABSTRACT

Described herein is a process for preparation of substituted pyridine dicarboxylate compounds.

8 Claims, No Drawings

PROCESS FOR PREPARATION OF FLUOROMETHYL-SUBSTITUTED PYRIDINE DICARBOXYLATES

REFERENCE TO RELATED APPLICATION

The present application is a continuation-in-part application of application Ser. No. 07/495,174 filed Mar. 19, 1990, now abandoned.

BACKGROUND OF THE INVENTION

The present invention relates to a process for preparing a lower alkyl 4-(lower alkyl)-2-difluoromethyl-6-trifluoromethyl-3,5-pyridinedicarboxylate by a catalytic dehydrofluorination of a lower alkyl 2,6-bis(trifluoromethyl)-1,4-dihydro-4-(lower alkyl)-3,5-pyridinedicarboxylate.

The present invention provides a novel and useful process of dehydrofluorination of certain dihydropyridine compounds to produce certain pyridine compounds having a difluoromethyl substituent in the 2-position and a trifluoromethyl substituent in the 6-position. The process involves using a catalytic amount of a water soluble organic catalyst, together with a water soluble inorganic base dissolved in water. The dihydropyridine is dissolved in an inert organic solvent. The resulting pyridine product has demonstrated superior preemergence control of grassy weeds in transplant rice and both preemergence and early postemergence control of crabgrass on lawn and turf areas.

DESCRIPTION OF THE PRIOR ART

Methods for preparation of 2,6-bis(fluorinated methyl)-pyridine dicarboxylates and pyridine dicarbothioates are disclosed in U.S. Pat. Nos. 4,692,184 and 4,618,679 and in European Patent 135,491. These compounds are useful as herbicides.

DESCRIPTION OF THE PRIOR ART

As used herein, the following terms have the following meanings:
DABCO - 1,4-diazabicyclo-[2.2.2]-octane
DBU - 1,8-diazabicyclo-[5.4.0]-undec-7-ene
ETFAA - ethyl 4,4,4-trifluoro-3-oxo-butanoate
IVA - isovaleraldehyde, or 3-methyl-butanal
NMR - nuclear magnetic resonance
GLC - gas-liquid chromatography
% Assay - weight % desired product compound
Yield - 100 ×mols desired product / 0.5 × mol initial ETFAA starting material.
NOTE: Where a yield is shown herein in discussing the effect of varying a process parameter, all process variables not explicitly shown to be varied are held constant.

As outlined in Scheme I, preparation of diethyl 2-difluoromethyl-4-(2-methylpropyl)-6-trifluoromethyl-3,5-pyridinedicarboxylate is accomplished by a Hantzsch-type base catalyzed intermolecular cyclization of ethyl 4,4,4-trifluoro-3-oxo-butanoate (ethyl trifluoroacetoacetate, or ETFAA) and isovaleraldehyde to form a substituted dihydroxypyran, followed by ammonolysis. Dehydration of the resultant dihydroxypiperidines gives a mixture of 1,4 and 3,4 dihydropyridine isomers. Dehydrofluorination of the dihydropyridines using an organic base such as DBU or 2,6-lutidine affords good yields (80% overall) of the pyridine diethylester.

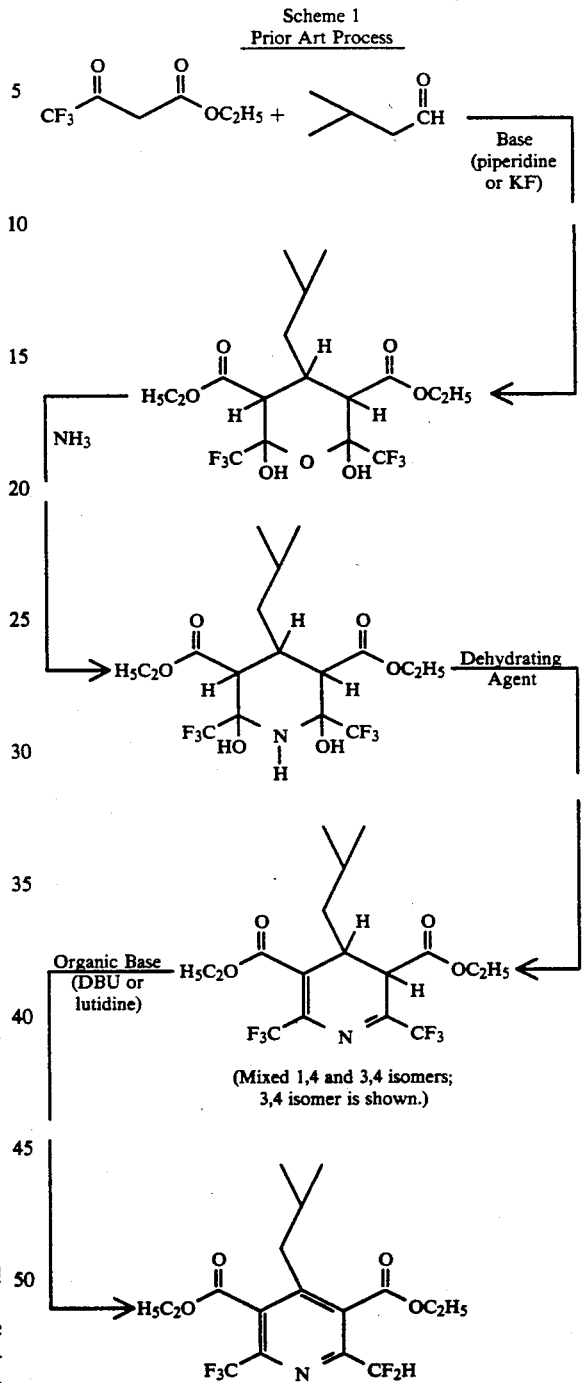

Scheme 1
Prior Art Process (Mixed 1,4 and 3,4 isomers; 3,4 isomer is shown.)

Examples 14 and 16 of U.S. Pat. No. 4,692,184 are reproduced below in relevant part and are illustrative of the prior art.

EXAMPLE 14 OF U.S. PAT. NO. 4,692,184

Preparation of dimethyl 2-(difluoromethyl)-6-(trifluoromethyl)-4-isobutyl-3,5-pyridinedicarboxylate (a) (a) Dehydrofluorination Using DBU:
A mixture of 23.0 g (0.0591 mole) of the dihydropyridine, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried (MgSO₄) and concentrated to give 14.4 g of an oil which, contained the desired product and acidic products. This oil is dissolved in ether and extracted with 100 ml of saturated sodium bicarbonate. The ether layer is dried (MgSO₄) and concentrated to give 8.9 g of an oil which is 71% pure desired product.

The sodium bicarbonate extract is acidified with concentrated HCl to give an oil which is extracted into ether. The ether layer is dried (MgSO₄) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from the dihydropyridine) of the desired product. The 71% pure desired product described previously was chromatographed by HPLC using 3% ethyl acetate/cyclohexane as eluent to give an earlier fraction (0.79 g, retention time 7–8.5 min) which was identified as methyl 6-(difluoromethyl)-4-(isobutyl)-2-(trifluoromethyl)-3-pyridinecarboxylate. The second fraction is an additional 6.4 g (29.4%) of pure pyridine product.

(b) Dehydrofluorination Using Tributylamine:

A mixture of 38.9 g of a 80% pure dihydropyridine and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to a 85% yield. This reaction can also be carried out in excess of tributylamine (10 equivalent) giving essentially similar results.

(c) Dehydrofluorination Using Tributylamine in Toluene:

A mixture of 38.9 g of 80% pure dihydropyridine, 20.4 of tributylamine and 30 ml of toluene is heated to 115° C. in 40 minutes and held at 115° C. for 1 hour and 40 minutes. The reaction mixture is cooled and worked up as in (b) to give 36.3 g of a 76% pure product which corresponds to a 90% yield.

(d) Dehydrofluorination Using Triethylamine:

A mixture of 11.8 g of 80% pure dihydropyridine and 3.34 g of triethylamine is heated at 100° C. for 10 minutes, then at 125° C. for 10 minutes. The reaction mixture was cooled and worked up as in (b) to give 8.14 g of a 76% pure product which corresponds to a 63% yield.

(e) Dehydrofluorination Using 2,6-Lutidine in the Presence of a Catalytic Amount Of DBU:

A mixture of 5.0 g of dihydropyridine and 2.13 g of 2,6-lutidine is heated at 143° C. for 30 minutes. Two drops of DBU is added and the reaction mixture is heated for an additional one hour and 30 minutes, cooled and worked up as in (b) to give 4.23 g of the desired product. The reaction can also be carried out in excess of 2,6-lutidine and catalytic amount of DBU without solvent or in the presence of toluene as solvent giving similar results.

EXAMPLE 16 OF U.S. PAT. NO. 4,692,184

Preparation of diethyl 2-(difluoromethyl)-4-isobutyl-6-(trifluoromethyl)-3,5-pyridinedicarboxylate A mixture of 10.0 g (0.0240 mole) of diethyl 2,6-bis)-trifluoromethyl)-1,4-dihydro-4-isobutyl-3,5-pyridinedicarboxylate, 3.65 g (0.0240 mole) of DBU and 150 ml of THF is held at reflux for 18 hours and concentrated. The residue is dissolved in ether and washed with diluted hydrochloric acid, dried (MgSO₄) and concentrated. The residue is kugelrohr distilled at 0.1 torr to give 4.80 g (50%) of the desired product.

SUMMARY OF THE INVENTION

In accordance with the present invention, a process is provided for the dehydrofluorination of a lower alkyl 2,6-bis(trifluoromethyl)-1,4-dihydro-4-(lower alkyl)-3,5-pyridinedicarboxylate to produce a lower alkyl 4-(lower alkyl)-2-difluoromethyl-6-trifluoromethyl-3,5-pyridinedicarboxylate comprising the steps of (a) bringing a lower alkyl 2,6-bis(trifluoromethyl)-1,4-dihydro-4-(lower alkyl)-3,5-pyridinedicarboxylate dissolved in an inert organic solvent into reactive contact with a catalytic amount of diazabicyclo-[2.2.2]-octane and with a sufficient amount of a water-soluble inorganic base in aqueous solution to insure substantially complete dehydrofluorination and to produce the corresponding water soluble fluoride salts of the inorganic base and the catalyst and to produce said dehydrofluorinated compound. The resulting aqueous phase and the organic phase are separated one from the other.

It is clear that the water soluble fluoride salts are mainly in the resulting aqueous phase. By a phase separation technique the produced fluoride salts are conveniently removed from the reaction medium leaving the desired pyridine in organic phase having minimal fluoride salts. Thus, the purification of the desired pyridine compound is significantly facilitated.

DESCRIPTION OF THE INVENTION

As in the Comparative Example above, the process of this invention is illustrated in detail below with reference to the preparation of the specific pyridine dicarboxylate compound prepared in Example 16 of U.S. Pat. No. 4,692,184.

To improve yield of the desired pyridine dicarboxylate product, the following process of the present invention generally employs the same reaction steps as Scheme I. According to the present invention, the final step of the process of Scheme I, dehydrofluorination of the dihydropyridines prepared in the previous step to afford the final pyridine dicarboxylate product, is accomplished by treatment with DABCO in contrast to the prior art dehydrofluorination step which employs DBU or 2,6-lutidine as the organic base.

In this process step, DABCO may be employed in either stoichiometric or catalytic amounts. Because DABCO is a difunctional base, the stoichiometric DABCO method uses at least one half mol of DABCO per mol of starting IVA. Use of about one mol of DABCO is preferred. The catalytic DABCO method, on the other hand, employs substantially less DABCO such as about 0.01 to less than 0.50, and preferably about 0.05 to about 0.20 mol DABCO per theoretical mol of dihydropyridines (i.e., per mol of original IVA) in conjunction with an amount of an additional base which is adequate to effect substantially complete dehydrofluorination. The additional base used in the process in which DABCO is employed as a catalyst is a base selected from the group consisting of KOH, NaOH, $K_2CO_3$, $Na_2CO_3$, $Ca(OH)_2$, triethylamine, and tributylamine. Use of a catalytic amount of DABCO thus may result in a substantial economic benefit in the process.

Whichever dehydrofluorination method is employed, it is desirable to have some water present in the process to act as a solvent for salts (such as, for example, the hydrofluoride salt of DABCO and/or of the additional base if one is used) which may be formed in the process.

Whichever specific dehydrofluorination method is used, it is desirable to conduct this process step in the presence of an inert solvent. Such solvents include, but are not limited to, benzene, toluene, xylenes, cyclohexane, monochlorobenzene, butyronitrile, and like solvents. Moreover, while the temperature used in this process step is not particularly critical, it is preferred to use temperatures in the range of 50° C. to 120° C., preferably 60° C. to 90° C.

In a particularly preferred embodiment using the catalytic DABCO dehydrofluorination method, the toluene solution from Step 2 is sparged vigorously with nitrogen to minimize formation of oxidation byproducts.

EXAMPLE 1

To a 3 l flask was added 444 g (1.06 mol) of diethyl 1,4-dihydro-4-(2-methylpropyl)-2,6-bis(trifluoromethyl)-3,5-pyridinedicarboxylate and 500 g of toluene. The solution was sparged subsurface with $N_2$ for 30 minutes. DABCO (10.3 g, 0.09 mol) was added as a solution in 18 g of water. $K_2CO_3$ (127 g, 0.9 mol) was then added as a solution in 144 g of water. An orange coloration developed on addition of the base. The reaction mixture was heated at 80° C. for 4.5 hours. During this time, the reaction was monitored bg GC to check for completion. Upon completion, the reaction mixture was cooled to 40° C. and the aqueous phase was removed from the vessel. Analysis of the reaction solution indicated the presence of 404 g (96% step yeield) of diethyl 2-difluoromethyl-4-(2-methylpropyl)-6-trifluoromethyl-3,5-pyridinedicarboxylate. The yield from ETFAA used as the starting material in preparation of they hydropyridine to this point was 83%.

The experimental procedure above is representative of the procedure for the catalytic use of DABCO in the dehydrofluorination reaction. Additional examples utilizing different bases and levels of catalyst are included below. The basis for charging catalyst and base as well as for calculating yields was the theoretical amount of dihydropyridine produced from the original starting material, ETFAA.

| Example | Mol % DABCO | Equiv. of base | | % yield |
|---|---|---|---|---|
| 2 | 10 | 1 | KOH | 80 |
| 3 | 7.5 | 1 | KOH | 82 |
| 4 | 3 | 1 | KOH | 79 |
| 5 | 5 | 0.63 | $K_2CO_3$ | 78 |
| 6 | 5 | 0.75 | $K_2CO_3$ | 77 |
| 7 | 7.5 | 0.75 | $K_2CO_3$ | 82 |
| 8 | 7.5 | 0.75 | $Na_2CO_3$ | 79 |
| 9 | 7.5 | 0.63 | $Ca(OH)_2$ | 75 |

EXAMPLE 2

4-(2-methylpropyl)-1,4-dihydro-3,5-pyridinedicarboxylic acid-, diethyl ester (24.0 mmol) was dissolved in 10 mL of toluene in a 50 mL 4-necked round bottom flask fitted with a stir bar, a reflux condenser, inert gas inlet, thermometer and connected to a pH meter. Nitrogen was sparged through the solution in the flask for 15 minutes. 1.8 mmol of DABCO was added to the contents of the flask which thereafter were heated to 80° C. while stirring. Then, 18.0 mmol of potassium carbonate dissolved in 2.5 mL water was added. At this point, the pH of the reaction mixture was measured to be 11.3. The stirring and heating of the contents were continued for 3 hours at which time the pH of the contents had dropped to 9.7. After cooling, the organic phase was separated from the aqueous phase. The toluene was stripped from the organic phase after being dried using $MgSO_4$ to provide 9.14 grams of a yellow oil. An analysis of the oil revealed that it was composed of 85.7% 2-difluoromethyl-6-trifluoromethyl-4-(2-methylpropyl)-3,5-pyridinedicarboxylic acid-, diethyl ester with a yield of 82.2%.

While the process of this invention has been specifically illustrated in terms of a specific pyridine dicarboxylate product, it is equally applicable to the preparation of other pyridine compounds. Selection of the aldehyde starting material will, of course, determine the substituent at the 4-position of the final pyridine product. Likewise it is evident that lower alkyl trifluoroacetoacetate esters other than the ethyl ester may equally well be employed. Accordingly, the scope of this invention is to be limited only in accordance with the annexed claims.

We claim:

1. A process of dehydrofluorination of a lower alkyl 2,6-bis(trifluoromethyl)-1,4-dihydro-4-(lower alkyl)-3,5-pyridinedicarboxylate to produce a lower alkyl 4-(lower alkyl)-2-difluoromethyl-6-trifluoromethyl-3,5-pyridinedicarboxylate, comprising the steps of (a) bringing a lower alkyl 2,6-bis(trifluoromethyl)-1,4-dihydro-4-(lower alkyl)-3,5-pyridinedicarboxylate dissolved in an inert organic solvent into reactive contact with a catalytic amount of 1,4-diazabicyclo-[2.2.2]-octane (DABCO) and with a sufficient amount of a water-soluble inorganic base in aqueous solution to insure substantially complete dehydrofluorination so as to produce the corresponding fluoride sales of the inorganic base and the catalyst and to produce said dehydrofluorinated compound and (b) phase separating the organic layer containing the dehydrofluorinated compound from the aqueous layer containing said fluoride salts.

2. A process according to claim 1 wherein that catalytic amount of DABCO is about 0.01 to less than 0.05 of the molar amount of the dihydropyridine reactant.

3. A process according to claim 1 wherein the catalytic amount of DABCO is about 0.05 to 0.20 of the molar amount of the dihydropyridine reactant.

4. A process according to claim 3 wherein the aprotic solvent is selected from benzene, toluene, xylenes, methylcyclohexane, monochlorobenzene, carbon tetrachloride, and butyronitrile.

5. A process according to claim 4 wherein the additional inorganic base is selected from the group consisting of $K_2CO_3$, $Na_2COphd 3$, $Ca(OH)_2$, KOH, and NaOH.

6. A process according to claim 5 wherein the additional inorganic base is $K_2CO_3$.

7. A process according to claim 3, wherein the process is conducted in the substantial absence of molecular oxygen.

8. A process according to any one of claims 2 to 7 wherein the pyridine dicarboxylic acid ester product is selected from 2-difluoromethyl-6-trifluoromethyl-4-(2-methylpropyl)-3,5-pyridinedicarboxylic acid, diethyl and dimethyl esters.

* * * * *